United States Patent
Lee et al.

(10) Patent No.: US 11,939,308 B2
(45) Date of Patent: Mar. 26, 2024

(54) BIPHENYL DERIVATIVE COMPOUND AND USE THEREOF

(71) Applicant: EWHA UNIVERSITY—INDUSTRY COLLABORATION FOUNDATION, Seoul (KR)

(72) Inventors: Kong Joo Lee, Seoul (KR); Hee-Yoon Lee, Daejeon (KR); Je Jin Lee, Seoul (KR); Hwang Suk Kim, Suwon-si (KR); Ji-Wan Seo, Daegu (KR); Hongsoo Lee, Daejeon (KR); Ji Soo Shin, Seoul (KR); Bo-kyung Kim, Incheon (KR)

(73) Assignee: EWHA University—Industry Collaboration Foundation, Seoul (KR)

( * ) Notice: Subject to any disclaimer, the term of this patent is extended or adjusted under 35 U.S.C. 154(b) by 132 days.

(21) Appl. No.: 17/059,754

(22) PCT Filed: May 30, 2019

(86) PCT No.: PCT/KR2019/006519
§ 371 (c)(1),
(2) Date: Nov. 30, 2020

(87) PCT Pub. No.: WO2019/231262
PCT Pub. Date: Dec. 5, 2019

(65) Prior Publication Data
US 2021/0214324 A1    Jul. 15, 2021

(30) Foreign Application Priority Data
May 30, 2018  (KR) .................. 10-2018-0062122

(51) Int. Cl.
| C07D 303/18 | (2006.01) |
| A23L 33/10 | (2016.01) |
| A61P 35/04 | (2006.01) |
| C07C 35/21 | (2006.01) |
| C07C 43/23 | (2006.01) |
| C07C 235/56 | (2006.01) |

(52) U.S. Cl.
CPC .......... *C07D 303/18* (2013.01); *A23L 33/10* (2016.08); *A61P 35/04* (2018.01); *C07C 35/21* (2013.01); *C07C 43/23* (2013.01); *C07C 235/56* (2013.01)

(58) Field of Classification Search
CPC .................................................. C07D 303/18
See application file for complete search history.

(56) References Cited

U.S. PATENT DOCUMENTS

2002/0156281 A1   10/2002 Booth
2021/0206706 A1*  7/2021 Lee .................. A61P 35/00

FOREIGN PATENT DOCUMENTS

CN      103980153 A    8/2014
WO    2014170706 A1   10/2014

OTHER PUBLICATIONS

Hori et al., "Dibenzothiophene and Related Compounds IV. Reactions of 5-Substitued 10,11-Dihydrodibenzo[b,f]thiepinium salts with Artllithiums", Chem. Pharma. Bull., vol. 22, pp. 2014-2019, Oct. 22, 1973 (Year: 1973).*
International Preliminary Report on Patentability, International Patent Application PCT/KR2019/006519, dated Dec. 20, 2020.
International Search Report (Translation), International Patent Application PCT/KR2019/006519, dated Sep. 5, 2019.
Written Opinion (Translation), International Patent Application PCT/KR2019/006519, dated Sep. 6, 2019.
R. Wakabayashi et al., "Synthesis of Phenanthrenes by Cationic Chromium(III) Porphyrin-Catalyzed Dehydration Cycloaromatization," Synlett, 24, 2297-2301 (2013).
M. Hori et al., "Dibenzothiophenes and Related Compounds. IV. Reactions of 5-Substituted 10,11-Dihydrodibenzo[b,f] hiepinium Salts with Aryllithiums," Chem. Pharm. Bull., 22(9), 2014-19 (1974).
J. Xi et al., "Efficient Synthesis of Phenanthridines Using Hendrickson Reagent Initiated Cascade Reaction under Mild Conditions," Synlett, 11, 1674-78 (2010).
P. Mamalis and V. Petrow, "142. Some Heterocyclic N-Oxides," J. Chem. Soc, 1950(1), 703-711 (1950).
J. Li and L. Ackermann, "Cobalt-Catalyzed C-H Arylations with Weakly-Coordinating Amides and Tetrazoles: Expedient Route to Angiotensin-11 Receptor Blockers," Chem. Eur. J., 21, 5718-22 (2015).
K.-H. Lin et al., "Activation of Antimetastatic Nm23-H1 Gene Expression by Estrogen and its alpha-Receptor," Endocrinology, 143(2), 467-75 (2002).

* cited by examiner

*Primary Examiner* — John S Kenyon
*Assistant Examiner* — Gillian A Hutter
(74) *Attorney, Agent, or Firm* — McDonnell Boehnen Hulbert & Berghoff LLP

(57) ABSTRACT

The present disclosure provides a novel biphenyl derivative compound or a pharmaceutically acceptable salt thereof. The biphenyl derivative compound or pharmaceutically acceptable salt thereof according to the present disclosure is a compound that increases Nm23-H1/NDPK activity and can inhibit cancer metastasis and growth. Thus, it exhibits excellent effects not only on the prevention, alleviation and treatment of cancer, but also on the suppression of cancer metastasis.

13 Claims, 3 Drawing Sheets

Blue: Nuclear, Red: F-actin

BIPHENYL DERIVATIVE COMPOUND AND USE THEREOF

CROSS-REFERENCE TO RELATED APPLICATIONS

This application is a U.S. National Stage entry of International Patent Application no. PCT/KR2019/006519, filed May 30, 2019, which claims the benefit of priority of Korean Patent Application no. 10-2018-0062122, filed May 30, 2018.

TECHNICAL FIELD

The present disclosure relates to a novel biphenyl derivative compound and the use thereof, and more particularly to a novel biphenyl derivative compound, a pharmaceutical composition for treating or preventing cancer containing the novel biphenyl derivative compound or a pharmaceutically acceptable salt thereof, a method for treating or preventing cancer comprising a step of administering the pharmaceutical composition, a composition for suppressing cancer metastasis containing the novel biphenyl derivative compound or a pharmaceutically acceptable salt thereof, a method for suppressing cancer metastasis comprising a step of administering the pharmaceutical composition, a food composition for preventing or alleviating cancer containing the novel biphenyl derivative compound or a pharmaceutically acceptable salt thereof, and the use of the biphenyl derivative compound or a pharmaceutically acceptable salt thereof in the manufacture of a medicament for treating cancer.

BACKGROUND ART

Tumor (cancer) metastasis is one of the most important factors determining the prognosis of cancer patients and is a major cause of cancer-related death. Although many efforts have been made to enable the survival of patients through cancer therapies, including surgery, radiotherapy and chemotherapy, efforts are still being made to increase the survival of cancer patients. The field of cancer metastasis research is one of the last strategies to overcome cancer, and research on cancer metastasis suppressors is essential in developing drugs for suppressing cancer metastasis.

Nm23 is a gene encoding a protein involved in the development and differentiation of normal tissue, and decreased expression of Nm23 in various metastatic cell lines has been reported. In general, Nm23 protein consisting of 150 to 180 amino acids contains a leucine zipper motif and has nucleoside diphosphate kinase (NDPK) activity. In particular, Nm23-H1 has been found to play an important role in cancer metastasis and other various cellular mechanisms, such as cell proliferation, embryonic development, differentiation, and tumor formation. Cancer metastasis occurs through a multi-step process in which cancer cells in a primary tumor tissue first invade blood vessels, and then move through the blood vessels, survive, and form new colonies at secondary sites. It has been found that Nm23, a nucleotide diphosphate kinase (NDPK), is a protein that converts NDPs (UDP, GDP, and CDP) to NTPs (UTP, GTP and CTP) using ATPs, and is an enzyme that regulates intracellular NTP levels. In addition, it has been found that overexpression of Nm23-H1 has a close relationship with decreased invasion of cancer cells. For example, WO01997-035024 discloses a method of treating cancer by administering a combination of enzymes including NDPK and a nucleoside analogue to cancer cells.

Based on this finding, studies have been conducted in the direction of increasing the expression of Nm23 or performing treatment with cell-permeable Nm23-H1. Specifically, it was confirmed that treatment with MPA (medroxyprogesterone acetate) increased the expression level of Nm23-H1. This phenomenon is understood as a mechanism by which cancer metastasis is suppressed by MPA treatment. However, since treatment with MPA causes unexpected intracellular responses in addition to raising the level of Nm23-H1, MPA has not been used as a drug.

In addition, in recent years, a method of suppressing cancer metastasis using cell-permeable Nm23-H1 has been proposed. Cell-permeable Nm23-H1 was introduced into cells in the form of a fusion with a transporter peptide that can pass through the cell membrane. As a result, it was confirmed that treatment with cell-permeable Nm23-H1 exhibited cancer metastasis suppressing activity. However, in order for such cell-permeable Nm23-H1 to be applied as a protein drug, the in vivo stability thereof remains as a challenge to be overcome. In addition, since drugs for suppressing cancer metastasis show no significant effect when they are used for treatment for a short period of time, there is a practical problem in that an expensive drug such as a protein drug cannot be chosen.

DISCLOSURE

Technical Problem

The present inventors have conducted extensive studies and made extensive efforts to develop agents capable of more effectively suppressing cancer development and metastasis, and as a result, have found that the use of newly developed biphenyl derivatives can prevent cancer development, treat developed cancer, and suppress metastasis of developed cancer, thereby completing the present disclosure.

Technical Solution

An object of the present disclosure is to provide a novel biphenyl derivative compound.

Another object of the present disclosure is to provide a pharmaceutical composition for treating or preventing cancer, the pharmaceutical composition containing the novel biphenyl derivative compound or a pharmaceutically acceptable salt thereof.

Still another object of the present disclosure is to provide a method for treating or preventing cancer, the method comprising a step of administering the pharmaceutical composition.

Yet another object of the present disclosure is to provide a pharmaceutical composition for suppressing cancer metastasis, the pharmaceutical composition containing the novel biphenyl derivative compound or a pharmaceutically acceptable salt thereof.

Still yet another object of the present disclosure is to provide a method for suppressing cancer metastasis, the method comprising a step of administering the pharmaceutical composition.

A further object of the present disclosure is to provide a food composition for preventing or alleviating cancer containing the novel biphenyl derivative compound or a pharmaceutically acceptable salt thereof.

Another further object of the present disclosure is to provide the use of the biphenyl derivative compound or a pharmaceutically acceptable salt thereof in the manufacture of a medicament for treating cancer.

Advantageous Effects

A novel biphenyl derivative compound of Formula 1 or a pharmaceutically acceptable salt thereof according to the present disclosure is an Nm23-H1/NDPK activity-increasing substance that may suppress cancer metastasis and growth. Therefore, the composition according to the present disclosure exhibits excellent effects not only on the prevention, alleviation and treatment of cancer, but also on the suppression of cancer metastasis.

BEST MODE

Figure 1:
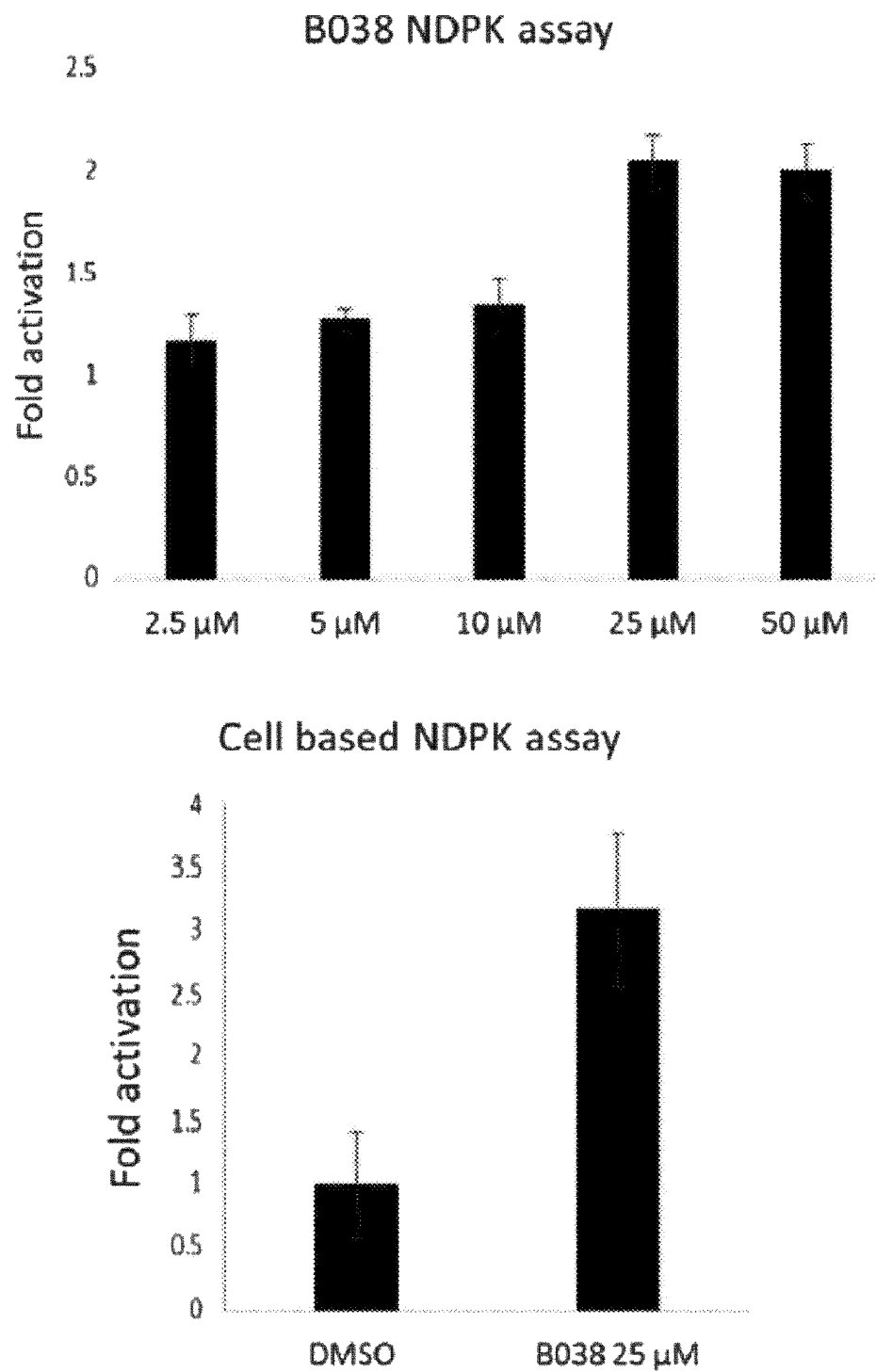
FIG. 1 shows the results of evaluating the NDPK activity-increasing effect of a compound (B038) of Example 1 at various concentrations.

To achieve the above-described objects, one aspect of the present disclosure provides a novel biphenyl derivative compound of the following Formula 1 or a pharmaceutically acceptable salt thereof:

[Formula 1]

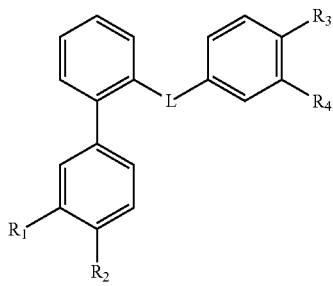

wherein
L is any one selected from the group consisting of —(C—C)—, —(NH—C(=O))—, —(C(=O)—NH)— and

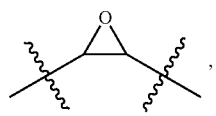 [SMILES: *C1OC1*]

and
$R_1$ to $R_4$ are each independently hydrogen, hydroxy or a $C_1$ to $C_3$ alkoxy group, wherein the $C_1$ to $C_3$ alkoxy group is any one selected from the group consisting of methoxy, ethoxy and propoxy groups.
Preferably, $R_1$ to $R_4$ in the compound of Formula 1 are each independently hydroxy or methoxy. More preferably, $R_1$ to $R_4$ in the compound of Formula 1 are each independently hydroxy or methoxy and have at least two methoxy groups.

In addition, according to an embodiment of the present disclosure, the compound of Formula 1 may be any one selected from the group consisting of the following compounds:

| Example | Structure |
|---|---|
| 1 | 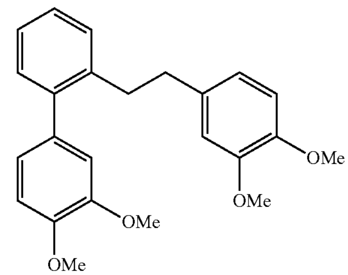 |
| 2 | 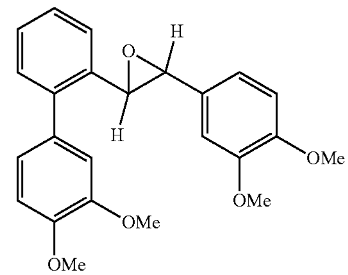 [SMILES: COc1ccc(-c2ccccc2C2OC2c2ccc(OC)c(OC)c2)cc1OC] |
| 3 | 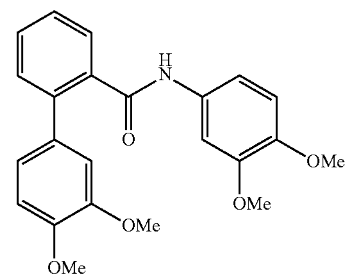 [SMILES: COc1ccc(NC(=O)c2ccccc2-c2ccc(OC)c(OC)c2)cc1OC] |
| 4 | 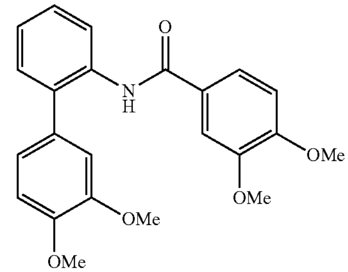 [SMILES: COc1ccc(C(=O)Nc2ccccc2-c2ccc(OC)c(OC)c2)cc1OC] |
| 5 | 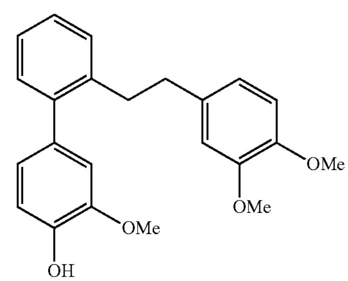 [SMILES: COc1cc(-c2ccccc2CCc2ccc(OC)c(OC)c2)ccc1O] |

| Example | Structure |
|---------|-----------|
| 6 | 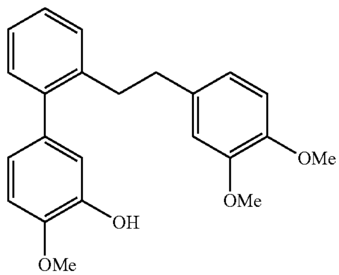 [SMILES: COc1ccc(-c2ccccc2CCc2ccc(OC)c(OC)c2)cc1O] |
| 7 | 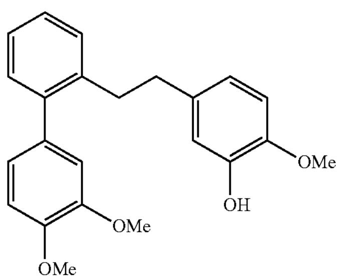 [SMILES: COc1ccc(CCc2ccccc2-c2ccc(OC)c(OC)c2)cc1O] |
| 8 | 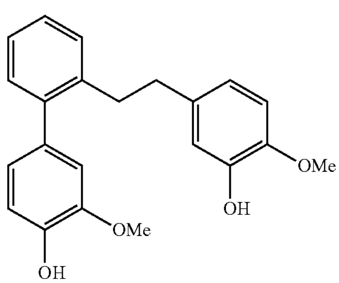 [SMILES: COc1ccc(CCc2ccccc2-c2ccc(O)c(OC)c2)cc1O] |
| 9 | 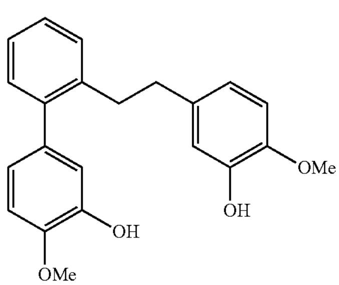 [SMILES: COc1ccc(CCc2ccccc2-c2ccc(OC)c(O)c2)cc1O] |
| 10 | 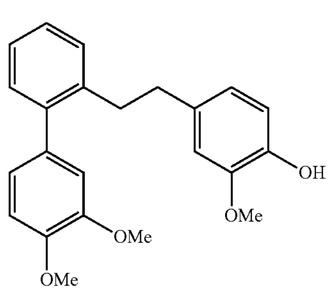 |

| Example | Structure |
|---------|-----------|
| 11 | 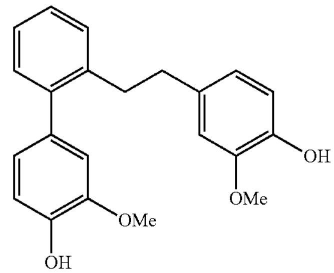 [SMILES: COc1cc(CCc2ccccc2-c2ccc(O)c(OC)c2)ccc1O] |

As used herein, the term "pharmaceutically acceptable salt" refers to salts which are commonly used in the pharmaceutical field. Examples of the salts include: inorganic ion salts formed with calcium, potassium, sodium, magnesium, etc.; inorganic acid salts formed with hydrochloric acid, nitric acid, phosphoric acid, bromic acid, iodic acid, perchloric acid, sulfuric acid, etc.; organic acid salts formed with acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts formed with methanesulfonic acid, ethanesulfonic acid, benzenesulfonic acid, p-toluenesulfonic acid, naphthalenesulfonic acid, etc.; amino acid salts formed with glycine, arginine, lysine, etc.; and amine salts formed with trimethylamine, triethylamine, ammonia, pyridine, picoline, etc. However, the types of salts meant in the present disclosure are not limited to the above listed salts.

Another aspect of the present disclosure provides a method for producing the biphenyl derivative compound of Formula 1.

The biphenyl derivative may be produced by a sequential or convergent synthetic route through the reaction route shown in Reaction Scheme 1, 2 or 3 below.

[Reaction Scheme 1]

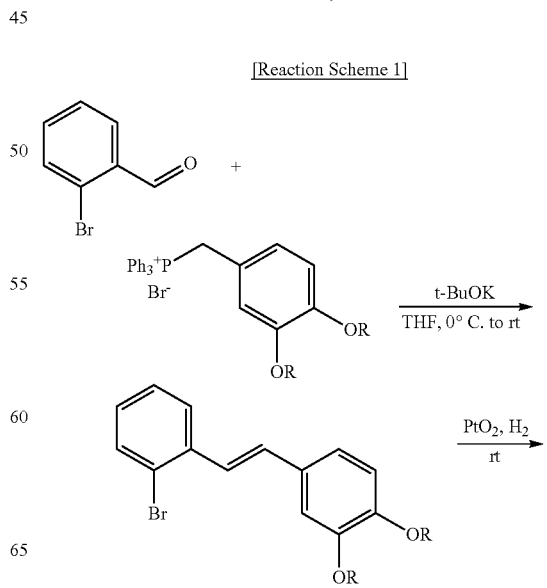

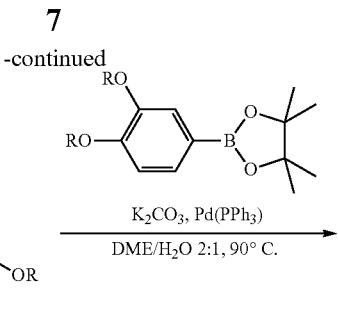

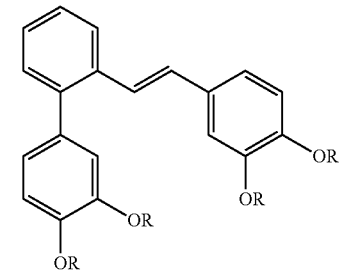

The compound of Formula 1 is produced by allowing a triphenylphosphonium bromide derivative to react with 2-bromobenzaldehyde, performing a reduction reaction with hydrogen in the presence of platinum oxide, and then performing a reaction with a boronic pinacol ester derivative, potassium carbonate and tetrakis(triphenylphosphine) palladium.

Thereby, compounds of Examples 5 to 11 may be produced.

In Reaction Scheme 1 above, Rs are each independently hydrogen or a $C_1$ to $C_3$ alkyl, preferably hydrogen or methyl.

[Reaction Scheme 2]

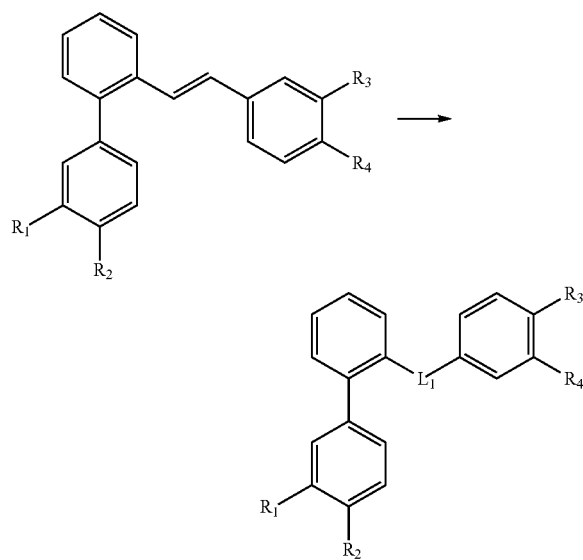

In Reaction Scheme 2 above, the compound of Example 1 may be synthesized by performing a reduction reaction with hydrogen in the presence of Pd/C.

In addition, in Reaction Scheme 2 above, a compound of Example 2 may be synthesized by performing a reaction after adding aqueous $NaHCO_3$ to 2-(3,4-dimethoxystyryl)-3'4'-dimethoxybiphenyl.

In Reaction Scheme 2 above, $R_1$ to $R_4$ are as defined in Formula 1, and $L_1$ is —(C—C)— or

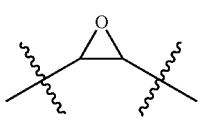

[Reaction Scheme 3]

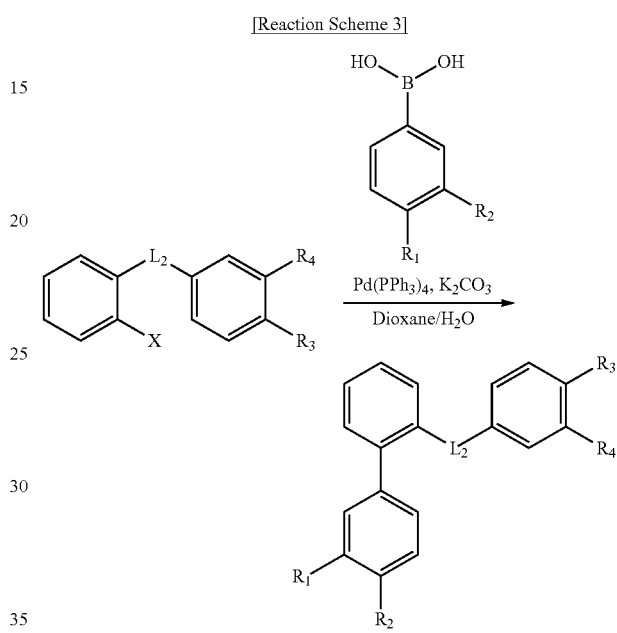

In Reaction Scheme 3 above, compounds of Examples 3 and 4 may be synthesized by allowing the above boronic acid derivative to react with a reactant after adding a Pd catalyst and potassium carbonate (3.0 eq.) to dioxane and distilled water.

In Reaction Scheme 3 above, $R_1$ to $R_4$ are as defined in Formula 1, and $L_2$ is —(NH—C(=O))—, or —(C(=O)—NH)—.

According to one embodiment of the present disclosure, the biphenyl derivative compound of Formula 1 may be produced according to the sequence shown in the Reaction Scheme, but may also be produced by the method presented herein or a similar method. Thus, the synthetic route thereof is not limited to the route shown in the Reaction Scheme. The starting materials are commercially available or may be prepared by methods similar to the methods presented below.

Isolation and purification of the biphenyl derivative compound or intermediate produced by the above-described method may be effected by any suitable separation or purification procedure that is used in the pharmaceutical field, for example, filtration, extraction, crystallization, column chromatography, thin-layer chromatography, thick-layer chromatography, preparative low or high pressure liquid chromatography or a combination of these procedures.

Still another aspect of the present disclosure provides a pharmaceutical composition for treating or preventing cancer, the pharmaceutical composition containing the biphenyl derivative compound of Formula 1 or a pharmaceutically acceptable salt thereof as an active ingredient.

In the present disclosure, the cancer is not particularly limited as long as it may be treated or prevented by the biphenyl derivative compound of Formula 1 or pharmaceutically acceptable salt thereof provided according to the present disclosure. In one example, the cancer may be breast cancer, lung cancer, melanoma, prostate cancer, colorectal cancer, bladder cancer, bone cancer, blood cancer, thyroid cancer, parathyroid cancer, bone marrow cancer, rectal cancer, throat cancer, laryngeal cancer, esophageal cancer, pancreatic cancer, stomach cancer, tongue cancer, skin cancer, brain tumor, uterine cancer, head or neck cancer, gallbladder cancer, oral cancer, colon cancer, anal cancer, central nervous system tumor, liver cancer, colorectal cancer, or the like. In another example, the cancer may be breast cancer, lung cancer, colorectal cancer, skin cancer, or the like.

According to one embodiment of the present disclosure, the biphenyl derivative compound of Formula 1 or a pharmaceutically acceptable salt thereof is a compound that increases Nm23-H1/NDPK activity, and may suppress cancer metastasis and growth.

Accordingly, the biphenyl derivative compound of Formula 1 or a pharmaceutically acceptable salt thereof exhibits effects not only on the prevention or treatment of cancer, but also on the suppression of cancer metastasis.

As used herein, the term "treating" refers to any action of alleviating or beneficially changing symptoms of cancer by administering the biphenyl derivative compound or a pharmaceutically acceptable salt thereof.

As used herein, the term "preventing" refers to any action of suppressing or delaying cancer by administering the biphenyl derivative compound or a pharmaceutically acceptable salt thereof.

The pharmaceutical composition of the present disclosure may contain the biphenyl derivative compound or a pharmaceutically acceptable salt thereof in an amount of 0.001 to 80 wt %, specifically 0.001 to 70 wt %, more specifically 0.001 to 60 wt %, based on the total weight of the composition, but is not limited thereto.

For administration, the pharmaceutical composition of the present disclosure may further contain at least one pharmaceutically acceptable carrier in addition to the biphenyl derivative compound of Formula 1 or a pharmaceutically acceptable salt thereof. As the pharmaceutically acceptable carrier, it is possible to use saline, sterile water, Ringer's solution, buffered saline, dextrose solution, maltodextrin solution, glycerol, ethanol, or a mixture of two or more thereof. If necessary, the pharmaceutical composition may contain other conventional additives such as an antioxidant, a buffer and a bacteriostatic agent. In addition, the pharmaceutical composition may be formulated as an injectable formulation, such as an aqueous solution, a suspension or an emulsion, or a pill, capsule, granule or tablet formulation by further adding a diluent, a dispersant, a surfactant, a binder and a lubricant. Thus, the pharmaceutical composition of the present disclosure may be in the form of a patch, a liquid, a pill, a capsule, granules, a tablet, a suppository, etc. These formulations may be prepared by any conventional method that is used for formulation in the art or by a method disclosed in Remington's Pharmaceutical Science (the latest edition), Mack Publishing Company, Easton Pa., and may be prepared in various forms depending on each disease or the components thereof.

The pharmaceutical composition of the present disclosure may be administered orally or parenterally (e.g., intravenously, subcutaneously, intraperitoneally or topically) according to a desired method, and the administration dose thereof may be in a wide range depending on the patient's body weight, age, sex, health condition and diet, the duration of administration, the mode of administration, excretion rate, and the severity of the disease. The compound of Formula 1 according to the present disclosure may be administered once or several times a day at a daily dose of about 1 to 1000 mg/kg, preferably 5 to 100 mg/kg.

The pharmaceutical composition of the present disclosure may further contain at least one active ingredient exhibiting a medicinal effect which is the same as or similar to that of the biphenyl derivative compound of Formula 1 or a pharmaceutically acceptable salt thereof, in addition to the biphenyl derivative compound of Formula 1 or a pharmaceutically acceptable salt thereof.

The present disclosure also provides a method for treating or preventing cancer, the method comprising a step of administering the biphenyl derivative compound, a pharmaceutically acceptable salt thereof or the pharmaceutical composition for treating or preventing cancer to a subject that is at risk of developing cancer or has developed cancer.

Here, the terms "biphenyl derivative compound", "pharmaceutically acceptable salt", "treating" and "preventing" are as defined above.

As used herein, the term "subject" refers to all animals, including humans, rats, mice and domestic animals that have developed cancer or are at risk of developing cancer. In a specific example, the subject may be mammals including humans.

The pharmaceutical composition of the present disclosure is administered in a pharmaceutically effective amount. The term "pharmaceutically effective amount" refers to an amount sufficient to treat a disease at a reasonable benefit/risk ratio applicable to any medical treatment. The effective dose level of the pharmaceutical composition may be determined depending on factors including the subject's type, disease severity, age and sex, the activity of the drug, sensitivity to the drug, the duration of administration, the route of administration, excretion rate, the duration of treatment, and drugs used in combination with the composition, as well as other factors well known in the medical field. For example, the biphenyl derivative compound or a pharmaceutically acceptable salt thereof may be administered at a daily dose of 0.01 to 500 mg/kg, specifically 10 to 100 mg/kg, and the administration may be performed once or several times a day.

The treatment method according to the present disclosure also encompasses inhibiting or averting symptoms of a disease as well as addressing the disease itself, prior to the onset of symptoms, by administering the compound of Formula 1. The prophylactic or therapeutic dose of a particular active ingredient in the management of a disease or condition may vary according to the nature and severity of the disease or condition and the route by which the active ingredient is administered. The dose and the dose frequency will also vary according to the age, body weight, and response of the individual patient. Suitable dosing regimens can be readily selected by those skilled in the art with due consideration of such factors. In addition, the treatment method according to the present disclosure may further comprise administering a therapeutically effective amount of an additional active agent helpful for the treatment of the disease together with the compound of Formula 1, in which the additional active agent may exhibit either a synergistic with the compound of Formula 1 or an assistant effect.

The present disclosure also provides a pharmaceutical composition for suppressing cancer metastasis, the pharmaceutical composition containing, as an active ingredient, the biphenyl derivative compound of Formula 1 or a pharmaceutically acceptable salt thereof. The present disclosure also provides a method for suppressing cancer metastasis, the method comprising a step of administering the composition for suppressing cancer metastasis to a subject that is at risk of cancer metastasis or has metastasized cancer.

Here, the terms "biphenyl derivative compound", "pharmaceutically acceptable salt", "treating", "preventing" and "subject" are as defined above.

The composition according to the present disclosure exhibits an excellent effect of suppressing cancer metastasis by increasing Nm23-H1/NDPK activity.

The present disclosure also provides a food composition for preventing or alleviating cancer, the food composition containing, as an active ingredient, the biphenyl derivative compound of Formula 1 or a pharmaceutically acceptable salt thereof.

The food composition of the present disclosure may be used as a health functional food. The term "health functional food" refers to a food manufactured and processed using raw materials or ingredients that have functionality beneficial for the human body in compliance with the Health Functional Food Act No. 6727. The term "functionality" means that the intake of food is directed to controlling nutriments on the structure and function of the human body or achieving useful effects on health such as physiological effects.

The food composition of the present disclosure may contain conventional food additives. Unless otherwise specified, the suitability as food additives is determined by the specification and standard of the concerned item in compliance with General Provisions and General Test Methods of the Korean Food Additives Codex approved by the Korean Food and Drug Administration.

The food composition of the present disclosure may contain the compound of Formula 1 in an amount of 0.01 to 95 wt %, preferably 1 to 80 wt %, based on the total weight of the composition, for the purpose of preventing and/or alleviating cancer. In addition, the food composition may be manufactured and processed in the form of tablets, capsules, powders, granules, liquids, pills, beverages, etc. for the purpose of preventing and/or alleviating cancer.

The present disclosure also provides the use of the biphenyl derivative compound of Formula 1 or a pharmaceutically acceptable salt thereof in the manufacture of a medicament for treating cancer.

The compound of Formula 1 for the manufacture of the medicament may be mixed with an acceptable adjuvant, diluent or carrier, etc., and may be combined with other active ingredients to form a combination formulation that exhibits a synergistic effect between the active ingredients.

The matters mentioned in the composition, use and treatment method of the present disclosure are equally applied unless they contradict each other.

MODE FOR INVENTION

Hereafter, examples of the disclosure will be described in detail so that the present disclosure can be easily carried out by those skilled in the art. However, the present disclosure may be embodied in various different forms and is not limited to the examples described herein.

In the following examples of the present disclosure, the reagents and solvents mentioned below are purchased from Sigma-Aldrich, TCI, unless otherwise specified, and HPLC was performed using a chiral IB column (Hex/iPA=80/20, 0.5 mL/min). As a silica gel for column chromatography, silica gel 60 (230-400 mesh ASTM) was used. $^1$H NMR data were measured using Bruker Fourier Transform AV300 (300 MHz) spectrometers, Bruker Fourier Transform AV400 (400 MHz) spectrometers or Agilent Technologies DD2 (600 MHz).

Example 1. Synthesis of 2-(3,4-dimethoxyphenethyl))-3',4'-dimethoxy-1,1'-biphenyl (HYL-NM-038)

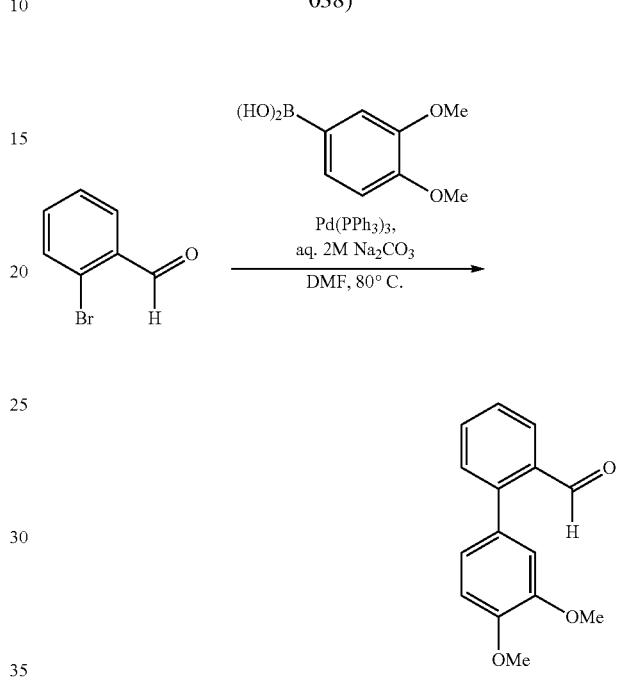

o-Bromobenzaldehyde (1.0 eq.) was dissolved in DMF, and then 3,4-dimethoxyphenylboronic acid (1.0 eq.), aqueous 2 M Na$_2$CO$_3$ (3.0 eq.) and Pd(PPh$_3$)$_4$ (0.01 eq.) were added thereto at room temperature. The mixture was stirred overnight 80° C. and then diluted with ethyl acetate. Next, the reaction was terminated by adding aqueous ammonium chloride and water thereto. Next, the reaction mixture was extracted with ethyl acetate, and the organic layer was dried with MgSO$_4$. The mixture was filtered, and the collected organic layer was concentrated and then purified on silica gel using column chromatography, thus synthesizing the desired compound.

$^1$H NMR (300 MHz, CDCl$_3$) δ 9.98 (s, 1H), 7.98 (d, J=7.9 Hz, 1H), 7.61 (td, J=7.5, 1.4 Hz, 1H), 7.45 (t, J=8.0 Hz, 2H), 6.98-6.85 (m, 3H), 3.93 (s, 3H), 3.89 (s, 3H).

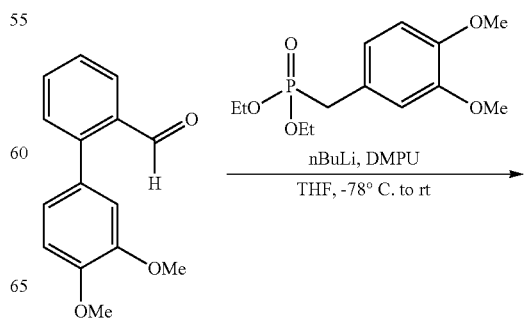

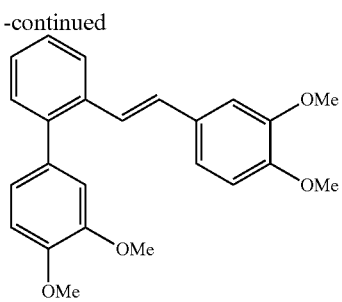

The above synthesized compound together with n-BuLi (2.48 M in Hx) (1.95 eq.) was added to a solution of dialkyl benzylphosphonate (2.0 eq.) in tetrahydrofuran at 0° C. The mixture was stirred at room temperature for 30 minutes and then cooled to a temperature of 0° C., and a solution of cis-aldehyde (1.0 eq.) and DMPU (5.0 eq.) in THF was added thereto using a cannula. The mixture was stirred overnight at room temperature, and then the reaction was terminated by adding aqueous ammonium chloride and water thereto. The reaction mixture was extracted with ethyl acetate, dried with $MgSO_4$, concentrated, and then purified on silica gel using column chromatography.

$^1$H NMR (599 MHz, $CDCl_3$) δ 7.70 (d, J=7.6 Hz, 1H), 7.33 (d, J=7.1 Hz, 2H), 7.30 (d, J=6.2 Hz, 1H), 7.03-6.91 (m, 6H), 6.89 (d, J=1.6 Hz, 1H), 6.80 (d, J=8.3 Hz, 1H), 3.92 (s, 3H), 3.86 (s, 3H), 3.84 (s, 3H), 3.83 (s, 3H).

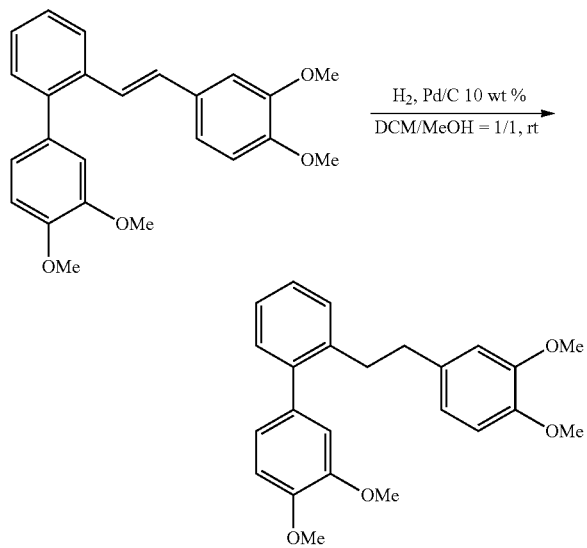

The above synthesized compound was dissolved in a 1:1 solvent of methanol and dichloromethane. After Pd/C (10 wt %) (0.1 eq.) was added thereto, the mixture was stirred under a hydrogen atmosphere for 3 hours. Thereafter, the stirred mixture was filtered through celite and silica, the organic solvent was evaporated off, and then the concentrated organic compound was purified on silica gel using column chromatography to afford the desired product [2-(3,4-dimethoxyphenethyl))-3',4'-dimethoxy-1,1'-biphenyl].

$^1$H NMR (300 MHz, Chloroform-d) δ 7.31-7.25 (m, 2H), 7.24-7.17 (m, 2H), 6.89 (d, J=8.6 Hz, 1H), 6.79 (dt, J=4.3, 2.2 Hz, 2H), 6.68 (d, J=8.1 Hz, 1H), 6.49 (dd, J=8.1, 2.0 Hz, 1H), 6.35 (d, J=2.0 Hz, 1H), 3.91 (s, 3H), 3.84 (s, 3H), 3.81 (s, 3H), 3.73 (s, 3H), 2.95-2.81 (m, 2H), 2.73-2.60 (m, 2H).

Example 2. Synthesis of 2-(3',4'-dimethoxy-[1,1'-biphenyl]-2-yl)-3-(3,4-dimethoxyphenyl)oxirane (HYL-NM-039)

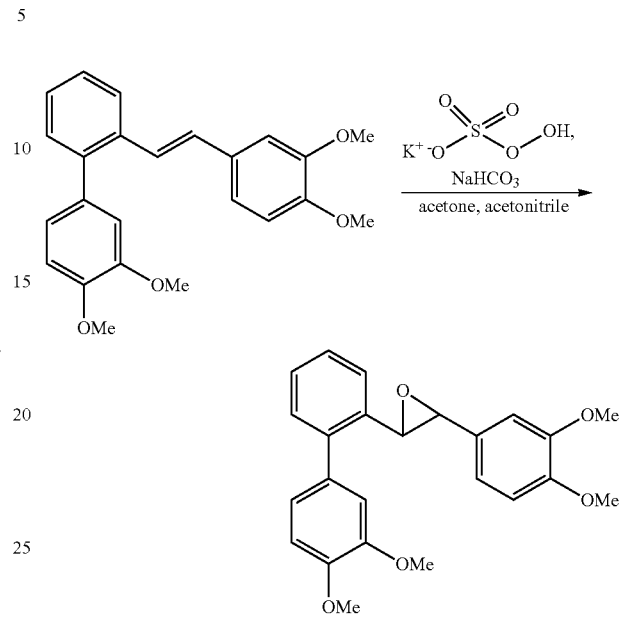

Aqueous $NaHCO_3$ was added to a solution of 2-(3,4-dimethoxystyryl)-3'4'-dimethoxybiphenyl (1.0 eq.) in acetone and acetonitrile and cooled to a temperature of 0° C. Oxone (2.2 eq.) was added thereto, followed by stirring for 4 hours. The reaction was terminated by adding distilled water thereto, and then the reaction mixture was extracted with ethyl acetate, dried with $MgSO_4$, and then concentrated. The resulting mixture was purified on silica gel using column chromatography. This afforded the desired product [2-(3',4'-dimethoxy-[1,1'-biphenyl]-2-yl)-3-(3,4-dimethoxyphenyl)oxirane].

$^1$H NMR (300 MHz, Benzene-d6) δ 7.84-7.76 (m, 1H), 7.50-7.37 (m, 3H), 7.27 (dd, J=7.1, 2.1 Hz, 2H), 7.07-6.85 (m, 4H), 6.61 (d, J=8.2 Hz, 1H), 6.50 (d, J=8.2 Hz, 1H), 3.40 (s, 3H), 3.36 (d, J=1.1 Hz, 6H), 3.33 (s, 3H).

Example 3. Synthesis of N-(3,4-dimethoxyphenyl)-3',4'-dimethoxy-[1,1'-biphenyl]-2-carboxamide (HYL-NM-041)

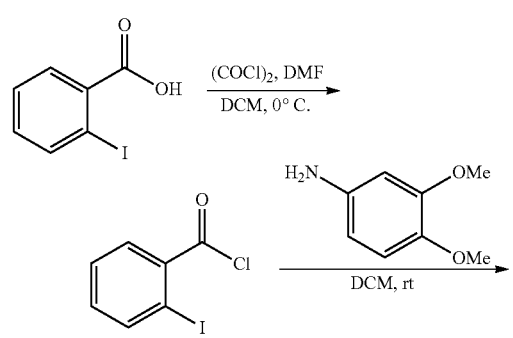

-continued

2 ml of DMF was added to a solution of 2-iodobenzoic acid (1.0 eq.) in dichloromethane at 0° C. Then, oxalyl chloride (2.0 eq.) was added thereto dropwise, followed by stirring for 1 hour. Next, 3,4-dimethoxyaniline was added to the mixture which was then warmed to room temperature and stirred for 2 and half hours. The reaction mixture was diluted with dichloromethane, and then the reaction was terminated by adding water thereto. The mixture was extracted with dichloromethane, dried with MgSO$_4$, and then concentrated under vacuum. Next, the concentrate was purified on silica gel using column chromatography to afford the desired product.

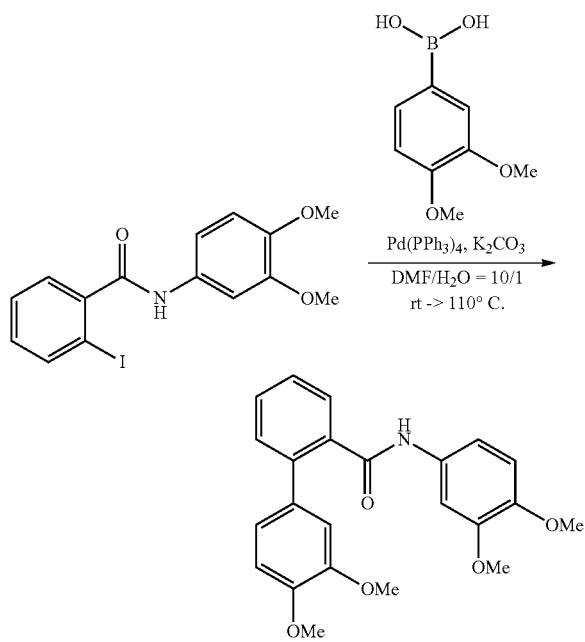

Tetrakis(triphenylphosphine)palladium (0.01 eq.) and K$_2$CO$_3$ (3.0 eq.) were added to a solution of N-(3,4-dimethoxyphenyl)-2-iodobenzamide (1.0 eq.) and 3,4-dimethoxyphenylboronic acid (2.0 eq.) in DMF (1 ml) and distilled water (0.1 ml) at room temperature. Then, the mixture was stirred at 110° C. for 16 hours. Next, the reaction was terminated by adding aqueous ammonium chloride thereto, and then the reaction mixture was extracted with ethyl acetate, dried with MgSO$_4$, and then concentrated under vacuum. Then, the concentrate was purified on silica gel using column chromatography to afford the desired product [N-(3,4-dimethoxyphenyl)-3',4'-dimethoxy-[1,1'-biphenyl]-2-carboxamide].

$^1$H NMR (300 MHz, Chloroform-d) δ 8.02 (s, 1H), 7.88 (dd, J=7.5, 1.6 Hz, 1H), 7.61-7.40 (m, 3H), 7.07 (dd, J=8.2, 2.1 Hz, 1H), 7.03-6.93 (m, 4H), 6.73 (d, J=8.6 Hz, 1H), 6.52 (dd, J=8.6, 2.5 Hz, 1H), 3.93 (s, 3H), 3.84 (d, J=2.2 Hz, 6H), 3.81 (s, 3H), 2.97 (s, 1H), 2.90 (s, 1H).

Example 4. Synthesis of N-(3',4'-dimethoxy-[1,1'-biphenyl]-2-yl)-3,4-dimethoxybenzamide (HYL-NM-042)

To a solution of 3,4-dimethoxybenzoic acid (1.0 eq.) in dichloromethane at 0° C., DMF was added in an amount equal to 1/10 of the dichloromethane. Oxalyl chloride (2.0 eq.) was added thereto dropwise, followed by stirring for 1 hour. The mixture was warmed to room temperature and then further stirred for 30 minutes. Thereafter, 2-iodoaniline (5.0 eq.) was added thereto, followed by further stirring for 2 hours. 5 mL of tetrahydrofuran was further added to the mixture, followed by further stirring for 30 minutes, and then the reaction was terminated by adding distilled water thereto. The mixture was extracted with dichloromethane, dried with MgSO$_4$, and then concentrated under vacuum. The concentrate was purified on silica gel using column chromatography to afford the desired product.

$^1$H NMR (300 MHz, Chloroform-d) δ 8.41 (dd, J=8.3, 1.6 Hz, 1H), 8.23 (s, 1H), 7.78 (dd, J=8.0, 1.5 Hz, 1H), 7.61-7.44 (m, 2H), 7.36 (ddd, J=8.6, 7.4, 1.5 Hz, 1H), 6.93 (d, J=8.2 Hz, 1H), 6.88-6.79 (m, 1H), 3.94 (s, 4H), 3.93 (s, 3H).

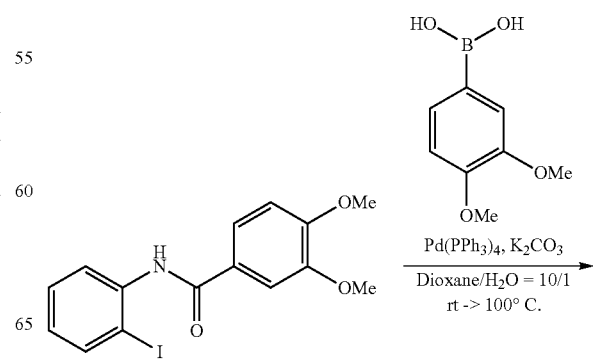

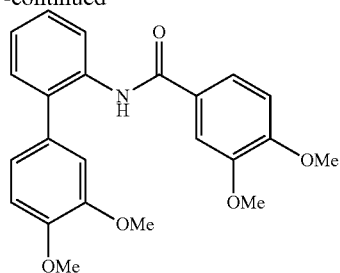

N-(2-iodophenyl)-3,4-dimethoxybenzamide (1.0 eq.), 3,4-dimethoxyboronic acid (2.0 eq.), a Pd catalyst (0.01 eq.) and potassium carbonate (3.0 eq.) were dissolved in dioxane and distilled water (10:1). The mixture was stirred at 100° C. for 13 hours, and then the reaction was terminated by adding aqueous ammonium chloride thereto. The organic mixture was extracted with ethyl acetate, dried with MgSO$_4$, and then concentrated under vacuum. Then, the concentrate was purified on silica gel using column chromatography to afford the desired product [N-(3',4'-dimethoxy-[1,1'-biphenyl]-2-yl)-3,4-dimethoxybenzamide].

$^1$H NMR (300 MHz, Chloroform-d) δ 8.50 (dd, J=8.1, 1.2 Hz, 1H), 8.04 (s, 1H), 7.39 (ddd, J=8.3, 7.2, 1.7 Hz, 1H), 7.32-7.22 (m, 2H), 7.16 (td, J=7.5, 1.3 Hz, 1H), 7.06-6.95 (m, 3H), 6.94-6.88 (m, 1H), 6.78 (d, J=8.4 Hz, 1H), 3.92 (s, 3H), 3.87 (s, 3H), 3.84 (s, 3H), 3.81 (s, 3H).

Examples 5 to 11. Synthesis of Compounds (HYL-NM-049 to 055)

General Procedure A

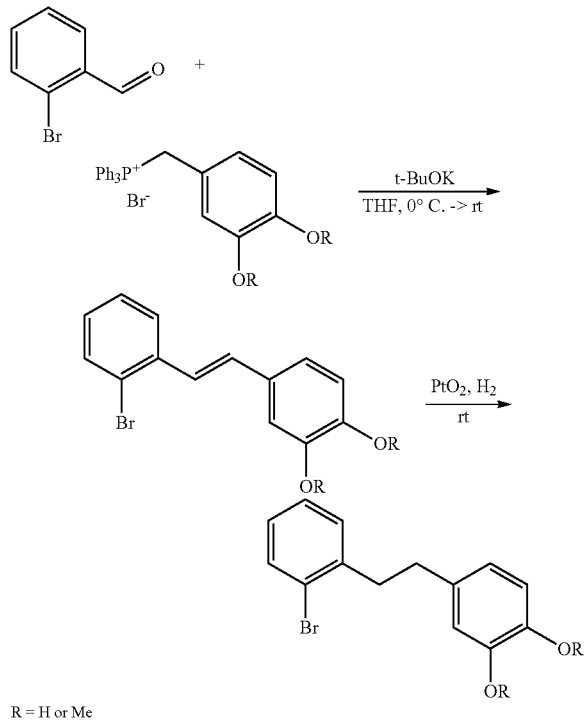

A triphenylphosphonium bromide derivative (1.2 eq.) was added to tetrahydrofuran at 0° C., and then t-BuOK (1.4 eq.) was added thereto. After 30 minutes, a solution of 2-bromobenzaldehyde (1.0 eq.) in tetrahydrofuran was added to the mixture over 10 minutes. The reaction mixture was warmed to room temperature and then stirred for 16 hours. Then, the reaction was terminated by adding distilled water thereto, and the reaction mixture was extracted with ethyl acetate. The extract was dried with MgSO$_4$, concentrated, and then purified on silica gel using column chromatography to afford the desired product.

The produced bromide (1 eq.) was dissolved in dichloromethane, and then platinum oxide (0.73 eq.) was added thereto under a hydrogen atmosphere. The mixture was stirred for 6 hours, filtered through silica and celite, and then concentrated under vacuum. The concentrate was purified on silica gel using column chromatography to afford the desired product.

General Procedure B

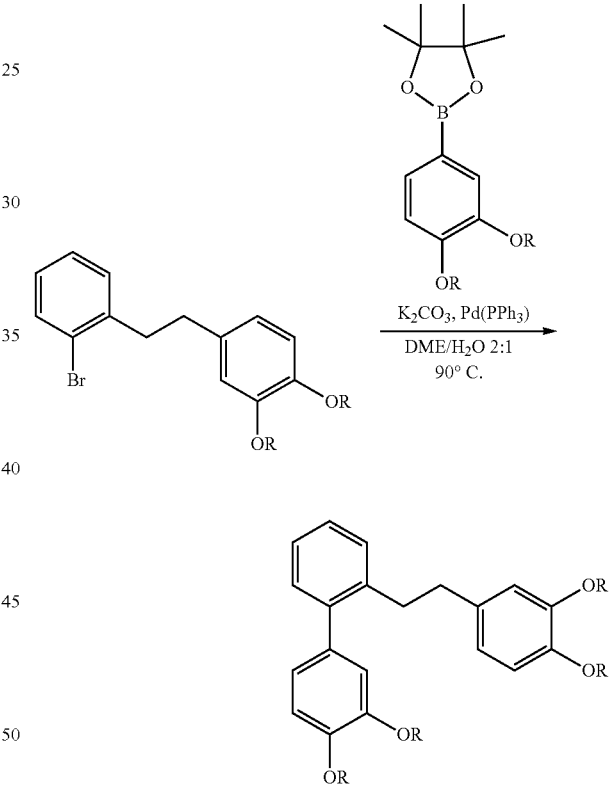

A boronic pinacol ester derivative (1.5 eq.), potassium carbonate (3.0 eq.) and tetrakis(triphenylphosphine)palladium (0.05 eq.) were dissolved in DME/distilled water (2/1). To the mixture, a solution of bromide (1.0 eq.) in DME was slowly added dropwise using a cannula. The mixture was mixed at 90° C. until the starting materials completely disappeared. After completion of the reaction, the reaction mixture was cooled to room temperature, and then the reaction was terminated by adding distilled water to the mixture. The reaction mixture was extracted with ethyl acetate and washed with brine. The organic mixture was dried with MgSO$_4$, concentrated, and then purified on silica gel using column chromatography to afford the desired product.

General Procedure C (Step of Producing Reactant of General Procedure A)

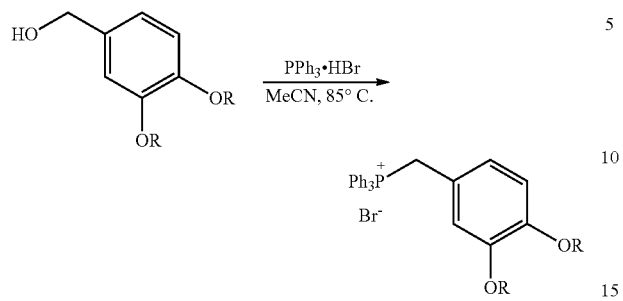

A solution of a benzyl alcohol derivative (1.0 eq.) and triphenylphosphine hydrogen bromide (1.0 eq.) in acetonitrile was stirred at 85° C. for 2 hours. When the product was produced as a salt, it was cooled to room temperature and then filtered. The product was washed with acetonitrile.

The following seven compounds were synthesized according to general procedures A, B and C using a reactant in which R at each position was correctly substituted with H or Me.

HYL-NM-49

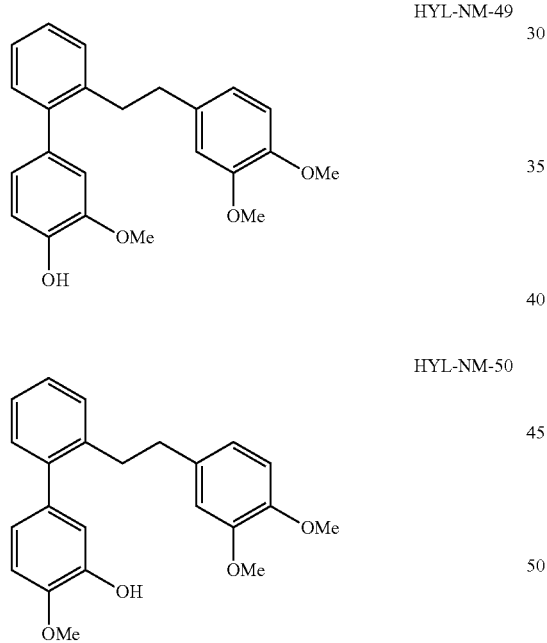

HYL-NM-50

HYL-NM-51

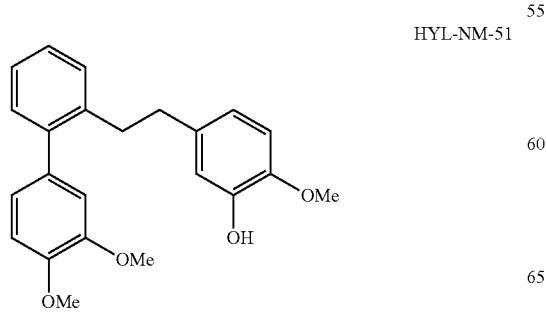

HYL-NM-52

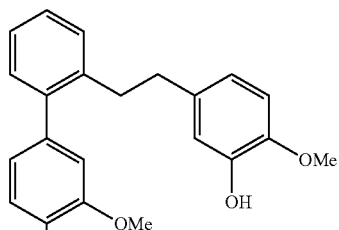

HYL-NM-53

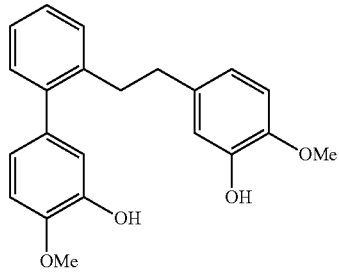 [SMILES: COc1ccc(CCc2ccccc2-c2ccc(OC)c(O)c2)cc1O]

HYL-NM-54

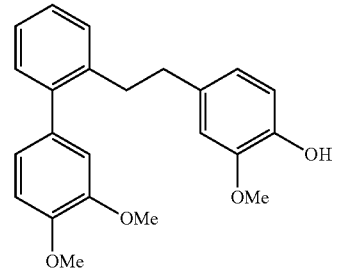

HYL-NM-55

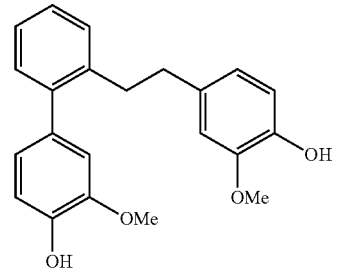 [SMILES: COc1cc(CCc2ccccc2-c2ccc(O)c(OC)c2)ccc1O]

Example 5. 2'-(3,4-dimethoxyphenethyl)-3-methoxy-[1,1'-biphenyl]-4-ol

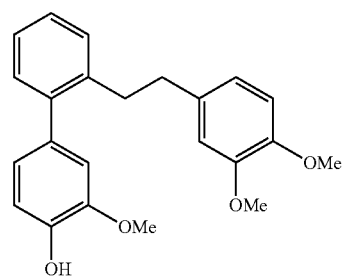

$^1$H NMR (400 MHz, Chloroform-d) δ 7.25 (d, J=2.5 Hz, 1H), 7.24-7.15 (m, 2H), 6.86 (dd, J=5.0, 3.1 Hz, 2H), 6.77-6.65 (m, 2H), 6.53 (dd, J=8.1, 1.9 Hz, 1H), 6.40 (d, J=2.0 Hz, 1H), 3.91 (s, 3H), 3.81 (d, J=1.1 Hz, 3H), 3.74 (s, 3H), 2.93-2.82 (m, 2H), 2.71-2.61 (m, 2H).

Example 6. 2'-(3,4-dimethoxyphenethyl)-4-methoxy-[1,1'-biphenyl]-3-ol

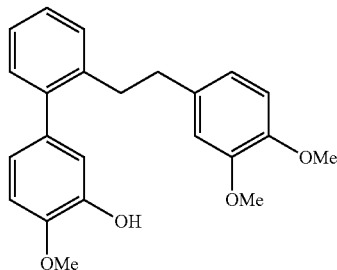

$^1$H NMR (400 MHz, Chloroform-d) δ 7.35-7.25 (m, 2H), 7.22-7.15 (m, 2H), 6.89-6.81 (m, 2H), 6.75-6.65 (m, 2H), 6.53 (dd, J=8.1, 2.0 Hz, 1H), 6.40 (d, J=2.0 Hz, 1H), 5.63 (s, 1H), 3.91 (s, 3H), 3.81 (s, 3H), 3.74 (s, 3H), 2.92-2.82 (m, 2H), 2.69-2.59 (m, 2H).

Example 7. 5-(2-(3',4'-dimethoxy-[1,1'-biphenyl]-2-yl)ethyl)-2-methoxyphenol

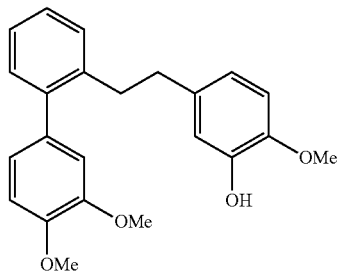

In general procedure B, boronic acid was used instead of pinacol boronic ester. The ratio between DME and H$_2$O used as the solvent was changed from 2:1 to 5:1.

$^1$H NMR (400 MHz, Chloroform-d) δ 7.29-7.25 (m, 2H), 7.23-7.18 (m, 1H), 6.90 (d, J=8.1 Hz, 1H), 6.85-6.77 (m, 2H), 6.69 (dd, J=15.1, 8.4 Hz, 1H), 6.57 (d, J=2.1 Hz, 1H), 6.51-6.39 (m, 1H), 3.92 (s, 3H), 3.84 (s, 3H), 3.82 (s, 3H), 2.96-2.73 (m, 2H), 2.69-2.54 (m, 2H).

Example 8. 2'-(3-hydroxy-4-methoxyphenethyl)-3-methoxy-[1,1'-biphenyl]-4-ol

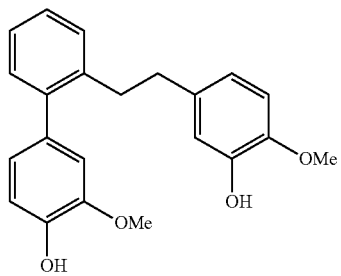 [SMILES: COc1ccc(CCc2ccccc2-c2ccc(O)c(OC)c2)cc1O]

$^1$H NMR (400 MHz, Chloroform-d) δ 7.29-7.23 (m, 2H), 7.22-7.16 (m, 2H), 6.90-6.83 (m, 2H), 6.76 (dd, J=8.2, 2.1 Hz, 1H), 6.68 (d, J=8.1 Hz, 1H), 6.58 (d, J=2.1 Hz, 1H), 6.48 (dd, J=8.2, 2.1 Hz, 1H), 5.65 (s, 1H), 5.52 (s, 1H), 3.93 (s, 3H), 3.82 (s, 3H), 2.92-2.78 (m, 2H), 2.72-2.57 (m, 2H).

Example 9. 2'-(3-hydroxy-4-methoxyphenethyl)-4-methoxy-[1,1'-biphenyl]-3-ol

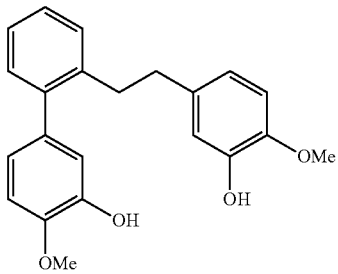 [SMILES: COc1ccc(CCc2ccccc2-c2ccc(OC)c(O)c2)cc1O]

$^1$H NMR (400 MHz, Chloroform-d) δ 7.27-7.24 (m, 2H), 7.23-7.15 (m, 2H), 6.91-6.84 (m, 2H), 6.76 (dd, J=8.2, 2.1 Hz, 1H), 6.68 (d, J=8.2 Hz, 1H), 6.58 (d, J=2.1 Hz, 1H), 6.48 (dd, J=8.2, 2.1 Hz, 1H), 5.65 (s, 1H), 5.52 (s, 1H), 3.92 (s, 3H), 3.82 (s, 3H), 2.96-2.74 (m, 2H), 2.74-2.58 (m, 2H).

Example 10. 4-(2-(3',4'-dimethoxy-[1,1'-biphenyl]-2-yl)ethyl)-2-methoxyphenol

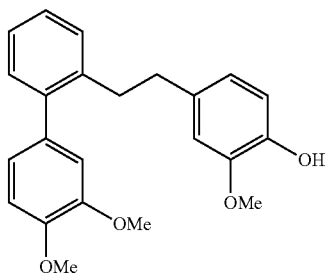

In general procedure B, boronic acid was used instead of pinacol boronic ester. The ratio between DME/H$_2$O used as the solvent was changed from 2:1 to 5:1.

$^1$H NMR (400 MHz, Chloroform-d) δ 7.36-7.25 (m, 2H), 7.24-7.14 (m, 2H), 6.93-6.85 (m, 1H), 6.82-6.75 (m, 2H), 6.72 (d, J=8.0 Hz, 1H), 6.44 (dd, J=8.0, 1.9 Hz, 1H), 6.31 (d, J=1.9 Hz, 1H), 5.40 (s, 1H), 3.90 (s, 3H), 3.84 (s, 3H), 3.73 (s, 3H), 2.90-2.79 (m, 2H), 2.70-2.55 (m, 2H).

Example 11. 2'-(4-hydroxy-3-methoxyphenethyl)-3-methoxy-[1,1'-biphenyl]-4-ol
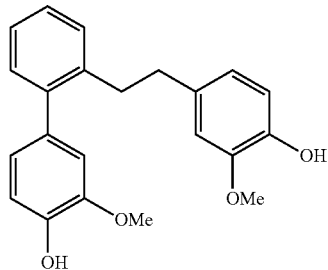
$^1$H NMR (400 MHz, Chloroform-d) δ 7.26-7.24 (m, 2H), 7.23-7.13 (m, 2H), 6.89-6.82 (m, 2H), 6.78-6.62 (m, 2H), 6.48 (dd, J=8.0, 2.0 Hz, 1H), 6.38 (d, J=1.9 Hz, 1H), 5.66 (s, 1H), 5.44 (s, 1H), 3.91 (s, 3H), 3.75 (s, 3H), 2.91-2.79 (m, 2H), 2.71-2.57 (m, 2H).
The structures of the compounds of the present disclosure, produced in Examples 1 to 11, are summarized in Table 1 below.

TABLE 1-continued

| Example | Structure |
|---|---|
| 9 | (structure with biphenyl-ethyl-phenyl; OMe, OH, OMe, OH substituents) |
| 10 | (structure with biphenyl-ethyl-phenyl; OMe, OMe, OMe, OH substituents) |
| 11 | (structure with biphenyl-ethyl-phenyl; OMe, OH, OH, OMe substituents) |

Example 12. Validation of Increased NDPK Activity

NDPK assay was performed by incubating 5 ng of recombinant Nm23-H1 with each of test compounds (Examples 1 to 3) in NDPK assay buffer (20 mM HEPES, 3 mM $MgCl_2$) at room temperature for 10 minutes, followed by reaction with 5 μM ADP for 1 minute.

The same effect was confirmed through cell-based NDPK assay, and the cell-based NDPK assay was performed as follows. 5,000K MDA-MB-231 cells were lysed with a protease inhibitor cocktail and an NDPK assay buffer, and the obtained cell lysate was centrifuged at 8,000 rpm at 4° C. for 10 minutes. 40 μL of the lysate was incubated with each test compound for 5 minutes, and then 50 μM UDP was added thereto, followed by reaction with NDPK. ATP consumption was assessed by an ATP determination kit (Molecular probe, USA).

The results are shown in Table 2 below.

TABLE 2

| Compound of Example | NDPK activity |
|---|---|
| 1 | 6.55 |
| 2 | 4.08 |
| 3 | 1.32 |
| 4 | 1.52 |
| 5 | 4 |

TABLE 2-continued

| Compound of Example | NDPK activity |
|---|---|
| 6 | 1.9 |
| 7 | 3.5 |
| 10 | 2.6 |

As shown above, it was confirmed that the compounds of the Examples exhibited an excellent effect of increasing NDPK activity (increasing Nm23-H1 activity).

Example 13. Validation of NDPK Activity-Increasing Effect of Compound of Example 1 at Various Concentrations The NDPK activity-increasing effect of the compound of Example 1 at various concentrations was evaluated in the same manner as in Example 2, and the results are shown in FIG. 1.

As shown in FIG. 1, it was confirmed that treatment with the compound of Example 1 exhibited an excellent effect of increasing NDPK activity even at low concentrations.

Example 14. Validation of Cancer Metastasis Suppression by Matrigel Invasion Assay Invasion assay was performed using a Transwell® unit (Corning, USA) with a polycarbonate membrane (pore size: 8 μm), with or without Matrigel coating. The membrane was coated with 50 μg Matrigel™-based membrane matrix (BD Bioscience, USA). $5 \times 10^4$ MDA-MB-231 cells were seeded into the upper chamber in a serum-free medium together with the compound of Example 1, and the lower chamber was filled with a medium containing 10% FBS. After incubation for 24 hours at 37° C., the cells on the upper side of the membrane were removed. The cells invading to the underside of the membrane were stained with 0.5% Crystal violet in 25% methanol and counted at 100-fold magnification under a microscope.

Figure 2A:
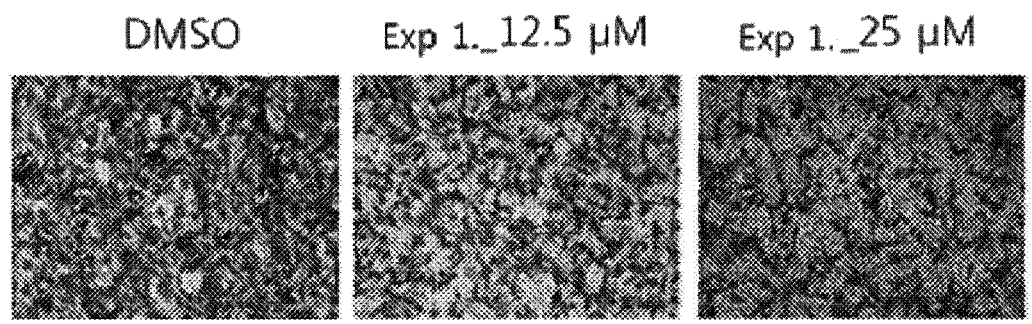
FIGS. 2A and 2B show the results of evaluating the invasion inhibitory effect of a compound (Exp. 1) of Example 1.
Figure 2B:
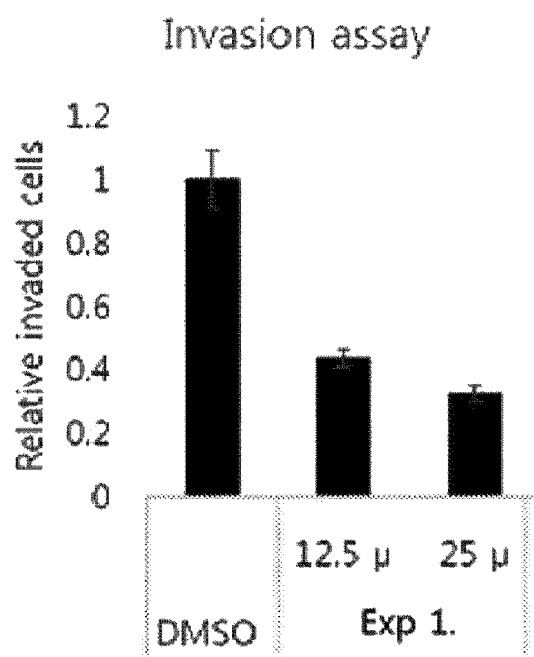

The results are shown in FIGS. 2A and 2B.

FIG. 2A shows micrographs, and FIG. 2B shows the results of counting invaded cells. As shown in FIGS. 2A and 2B, it was confirmed that treatment with the compound of Example 1 significantly suppressed cell invasion.

Example 15. Validation of Cancer Metastasis Suppression by Immunofluorescent Staining Assay MDA-MB-231 cells were grown on the Secureslip™ (Sigma) cell culture glass cover slip to a confluence of 50 to 70%, and then treated with or without the compound of Example 1 (B038) for various times. The cells were gently washed with cold HBSS, and then fixed with 4% paraformaldehyde-containing HBSS in RBS for 10 minutes at room temperature. After washing with HBSS, permeabilization with 0.1% Triton X-100 was performed for 10 minutes at room temperature. After washing twice with HBSS, the cells were blocked with 3% BSA, 0.2% Tween20 and 0.2% gelatin in HBSS for 1 hour at room temperature, and incubated with primary antibody at 37° C. for 2 hours. F-actin was stained by Rhodamine-Phalloidin (Thermo Fisher Scientific) for 2 hours at 37° C., followed by washing 3 times with HBSS for 20 minutes. Coverslips were mounted with an anti-fading solution and viewed using an ×63 objective lens of an LSM510 META (Zeiss) laser scanning confocal microscope.

Figure 3:
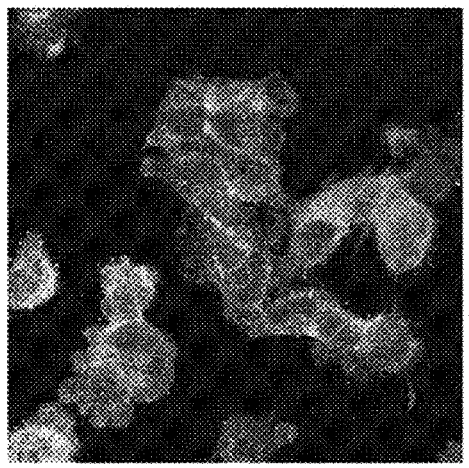
FIG. 3 shows the results of confirming the suppression of cancer cell metastasis by treatment with a compound of Example 1.
Figure 3:
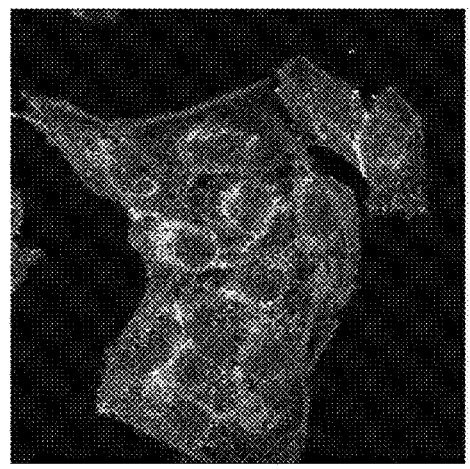

The results are shown in FIG. 3.

As shown in FIG. 3, from localization of F-actin in the MDA-MB-231 cells, it could be confirmed that ruffles decreased and cell-to-cell contact increased (B038). This suggests that the compound of Example 1 suppresses cancer cell metastasis by inhibiting the activity of Rac1 involved in cell migration via Nm23-H1 and reducing cell migration.

Taking the above results together, the novel biphenyl derivative compounds according to the present disclosure suppressed cancer metastasis by increasing NDPK activity. That is, the novel compounds according to the present disclosure may exhibit an excellent effect of suppressing cancer metastasis, and thus be used as anticancer agents and anticancer adjuvants that exhibit excellent preventive and therapeutic effects.

Although the present disclosure has been described in detail with reference to the specific features, it will be apparent to those skilled in the art that this detailed description is only of a preferred embodiment thereof, and does not limit the scope of the present disclosure. Thus, the substantial scope of the present disclosure will be defined by the appended claims and equivalents thereto.

The invention claimed is:

1. A biphenyl derivative compound of the following Formula 1 or a pharmaceutically acceptable salt thereof:

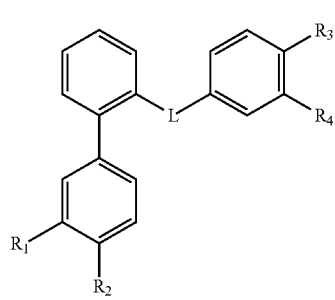

[Formula 1]

wherein
L is —(CH$_2$—CH$_2$)—, and
each of R$_1$, R$_2$, R$_3$ and R$_4$ is independently hydroxy or methoxy.

2. The biphenyl derivative compound or pharmaceutically acceptable salt thereof according to claim 1, wherein at least two of R$_1$, R$_2$, R$_3$ and R$_4$ are methoxy groups.

3. The biphenyl derivative compound or pharmaceutically acceptable salt thereof according to claim 1, wherein the compound of Formula 1 is selected from among the following compounds:

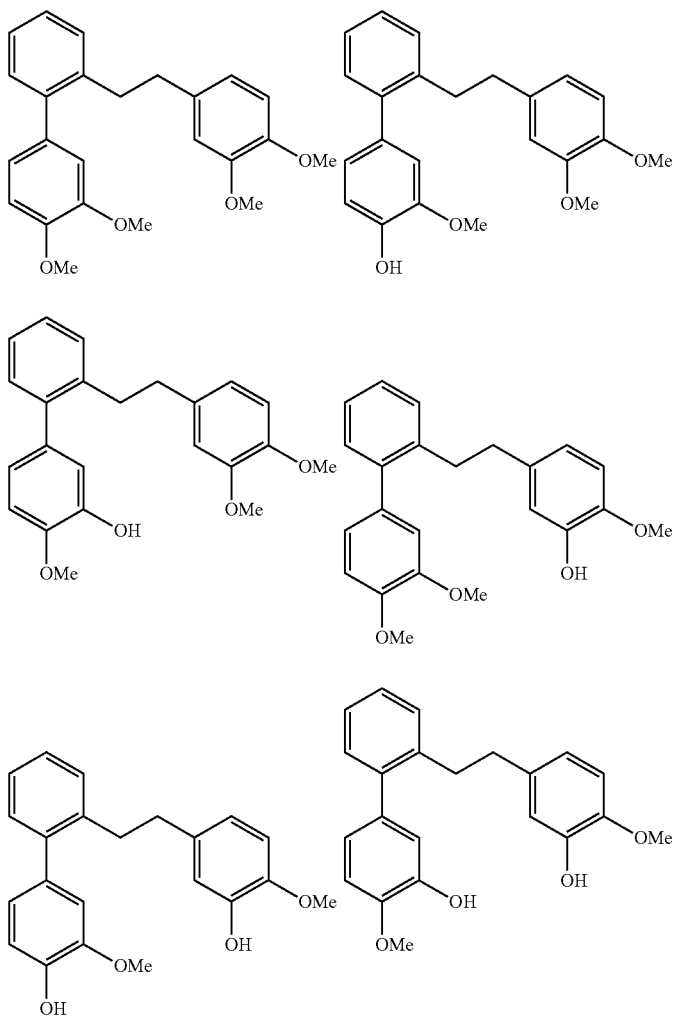

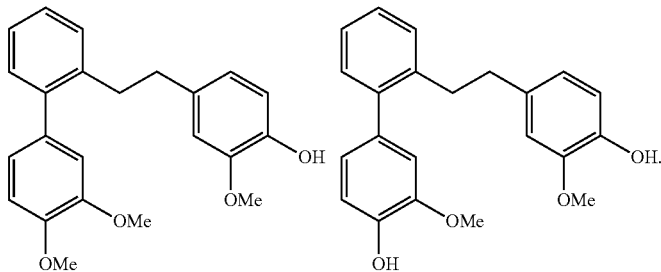

4. A pharmaceutical composition for treating or preventing cancer, the pharmaceutical composition containing, as an active ingredient, the biphenyl derivative compound or pharmaceutically acceptable salt thereof according to claim 1.

5. The pharmaceutical composition of claim 4, wherein the cancer is cancer selected from the group consisting of breast cancer, lung cancer, melanoma, prostate cancer, colorectal cancer, bladder cancer, bone cancer, blood cancer, thyroid cancer, parathyroid cancer, bone marrow cancer, rectal cancer, throat cancer, laryngeal cancer, esophageal cancer, pancreatic cancer, stomach cancer, tongue cancer, skin cancer, brain tumor, uterine cancer, head or neck cancer, gallbladder cancer, oral cancer, colon cancer, anal cancer, central nervous system tumor, liver cancer, colorectal cancer, and combinations thereof.

6. The pharmaceutical composition of claim 4, wherein the cancer is cancer selected from the group consisting of breast cancer, lung cancer, colorectal cancer, and skin cancer.

7. A method for treating or preventing cancer, the method comprising a step of administering the pharmaceutical composition according to claim 4 to a subject that is at risk of developing cancer or has developed cancer.

8. A composition for suppressing cancer metastasis, the composition containing, as an active ingredient, the biphenyl derivative compound or pharmaceutically acceptable salt thereof according to claim 1.

9. A method for suppressing cancer metastasis, the method comprising a step of administering the composition according to claim 8 to a subject that is at risk of cancer metastasis or has metastasized cancer.

10. A food composition for preventing or alleviating cancer, the food composition containing, as an active ingredient, the biphenyl derivative compound or pharmaceutically acceptable salt thereof according to claim 1.

11. The method according to claim 7, wherein the cancer is cancer selected from the group consisting of breast cancer, lung cancer, melanoma, prostate cancer, colorectal cancer, bladder cancer, bone cancer, blood cancer, thyroid cancer, parathyroid cancer, bone marrow cancer, rectal cancer, throat cancer, laryngeal cancer, esophageal cancer, pancreatic cancer, stomach cancer, tongue cancer, skin cancer, brain tumor, uterine cancer, head or neck cancer, gallbladder cancer, oral cancer, colon cancer, anal cancer, central nervous system tumor, liver cancer, colorectal cancer, and combinations thereof.

12. The method according to claim 7, wherein the cancer is cancer selected from the group consisting of breast cancer, lung cancer, colorectal cancer, and skin cancer.

13. A method for treating or preventing cancer, the method comprising a step of administering a pharmaceutical composition containing, as an active ingredient, the biphenyl derivative compound or pharmaceutically acceptable salt thereof according to claim 3 to a subject that is at risk of developing cancer or has developed cancer.

\* \* \* \* \*